US009344815B2

(12) United States Patent
Selig et al.

(10) Patent No.: US 9,344,815 B2
(45) Date of Patent: May 17, 2016

(54) METHOD FOR AUGMENTING HEARING

(71) Applicant: Symphonic Audio Technologies Corp., San Francisco, CA (US)

(72) Inventors: Aaron Alexander Selig, San Francisco, CA (US); Varun Srinivasan, San Francisco, CA (US)

(73) Assignee: Symphonic Audio Technologies Corp., San Francisco, CA (US)

( * ) Notice: Subject to any disclaimer, the term of this patent is extended or adjusted under 35 U.S.C. 154(b) by 0 days.

(21) Appl. No.: 14/178,067

(22) Filed: Feb. 11, 2014

(65) Prior Publication Data
US 2014/0314261 A1 Oct. 23, 2014

Related U.S. Application Data

(60) Provisional application No. 61/763,182, filed on Feb. 11, 2013, provisional application No. 61/867,449, filed on Aug. 19, 2013, provisional application No. 61/880,377, filed on Sep. 20, 2013.

(51) Int. Cl.
*H04R 25/00* (2006.01)
*A61B 5/00* (2006.01)
*A61B 5/12* (2006.01)
*H04M 1/725* (2006.01)
*H04R 29/00* (2006.01)

(52) U.S. Cl.
CPC ............... *H04R 25/50* (2013.01); *A61B 5/123* (2013.01); *A61B 5/6898* (2013.01); *H04M 1/72569* (2013.01); *H04M 1/72591* (2013.01); *H04R 25/70* (2013.01); *A61B 2560/0242* (2013.01); *H04R 29/008* (2013.01); *H04R 2225/41* (2013.01); *H04R 2225/55* (2013.01); *H04R 2225/83* (2013.01); *H04R 2460/03* (2013.01); *H04R 2460/07* (2013.01)

(58) Field of Classification Search
CPC ...... H04R 25/70; H04R 25/30; H04R 25/554; H04R 2225/025; H04R 25/606; H04R 2460/13; H04R 2225/67; H04R 2225/43; H04R 25/558; A61B 5/123; A61B 5/125; A61N 1/36032; A61N 1/0541; H04W 4/06; H04H 60/37
USPC .............. 381/60, 312–331, 341; 600/25, 559; 607/56–57; 455/3.06
See application file for complete search history.

(56) References Cited

U.S. PATENT DOCUMENTS

| 6,813,490 B1 | 11/2004 | Lang et al. | |
|---|---|---|---|
| 6,853,850 B2 | 2/2005 | Shim et al. | |
| 2002/0100044 A1* | 7/2002 | Daniels | H04N 5/44543 725/39 |
| 2003/0003864 A1 | 1/2003 | Locke | |

(Continued)

*Primary Examiner* — Rasha Al Aubaidi
(74) *Attorney, Agent, or Firm* — Jeffrey Schox; Ivan Wong

(57) ABSTRACT

One variation of a method for augmenting sound includes: at a mobile computing device and a connected audio output device, outputting a tone in a hearing test; based on a response to the tone entered by a user, generating a hearing profile for the user and corresponding to the mobile computing device and the audio output device; receiving an audio signal; qualifying the audio signal as a particular audio type from a set of audio types; selecting, from a set of sound profiles, a particular sound profile corresponding to the particular audio type; at the mobile computing device, transforming the audio signal into a processed audio signal according to the particular sound profile and the hearing profile of the user; and outputting the processed audio signal at the connected audio output device.

18 Claims, 5 Drawing Sheets

(56) References Cited

U.S. PATENT DOCUMENTS

| | | |
|---|---|---|
| 2004/0102931 A1* | 5/2004 | Ellis .................... A61B 5/1038 702/188 |
| 2005/0260985 A1 | 11/2005 | Rader et al. |
| 2006/0112123 A1 | 5/2006 | Clark et al. |
| 2007/0255435 A1 | 11/2007 | Cohen et al. |
| 2008/0208820 A1 | 8/2008 | Usey et al. |
| 2009/0076825 A1 | 3/2009 | Bradford et al. |
| 2009/0154745 A1 | 6/2009 | Latzel |
| 2009/0180631 A1 | 7/2009 | Michael et al. |
| 2010/0119093 A1 | 5/2010 | Uzuanis et al. |
| 2010/0145134 A1 | 6/2010 | Madsen |
| 2010/0191143 A1 | 7/2010 | Ganter et al. |
| 2011/0153603 A1 | 6/2011 | Adiba et al. |
| 2011/0191361 A1 | 8/2011 | Gupta et al. |
| 2011/0280409 A1 | 11/2011 | Michael et al. |
| 2011/0280422 A1* | 11/2011 | Neumeyer et al. ............ 381/314 |
| 2011/0293123 A1* | 12/2011 | Neumeyer et al. ............ 381/314 |
| 2011/0300806 A1 | 12/2011 | Lindahl et al. |
| 2012/0021808 A1 | 1/2012 | Tseng |
| 2012/0057078 A1 | 3/2012 | Fincham |
| 2012/0110004 A1 | 5/2012 | Meijer |
| 2012/0183163 A1* | 7/2012 | Apfel ............................ 381/314 |
| 2012/0306631 A1 | 12/2012 | Hughes |
| 2012/0311581 A1 | 12/2012 | Balmin et al. |
| 2013/0052956 A1 | 2/2013 | McKell |
| 2013/0142366 A1* | 6/2013 | Michael et al. ............... 381/314 |
| 2013/0151563 A1 | 6/2013 | Addepalli et al. |
| 2013/0177189 A1* | 7/2013 | Bryant et al. ................. 381/315 |
| 2014/0314261 A1 | 10/2014 | Selig et al. |
| 2014/0334644 A1 | 11/2014 | Selig et al. |
| 2014/0379343 A1 | 12/2014 | Karimi-Cherkandi et al. |
| 2015/0078575 A1 | 3/2015 | Selig et al. |

* cited by examiner

METHOD FOR AUGMENTING HEARING

CROSS-REFERENCE TO RELATED APPLICATIONS

This application claims the benefit of U.S. Provisional Application No. 61/763,182, filed on 11 Feb. 2013, U.S. Provisional Application No. 61/867,449, filed on 19 Aug. 2013, and U.S. Provisional Application No. 61/880,377, filed on 20 Sep. 2013, all of which are incorporated in their entireties by this reference.

TECHNICAL FIELD

This invention relates generally to the field of hearing augmentation, and more specifically to a new and useful method for augmenting hearing in the field of hearing augmentation.

BACKGROUND

Approximately 12% of the population in the United States suffers from significant hearing loss. 30-40% of people over the age of 65, 14% of people between the ages of 45-64, and 15% of children between the ages of 6-19 having a measurable degree of hearing loss in at least one ear. However, though hearing aids can offer dramatic improvement in hearing for people with hearing loss in specific settings, hearing aids are typically limited to single hearing profiles and therefore fail to adequately augment user hearing in multiple use scenarios and during varying physical settings.

Therefore, there is a need in the field of hearing augmentation to create a new and useful method for augmenting hearing. This invention provides such a new and useful method.

DESCRIPTION OF THE EMBODIMENTS

The following description of the embodiments of the invention is not intended to limit the invention to these embodiments, but rather to enable any person skilled in the art to make and use this invention.

1. Method and Applications

Figure 1:
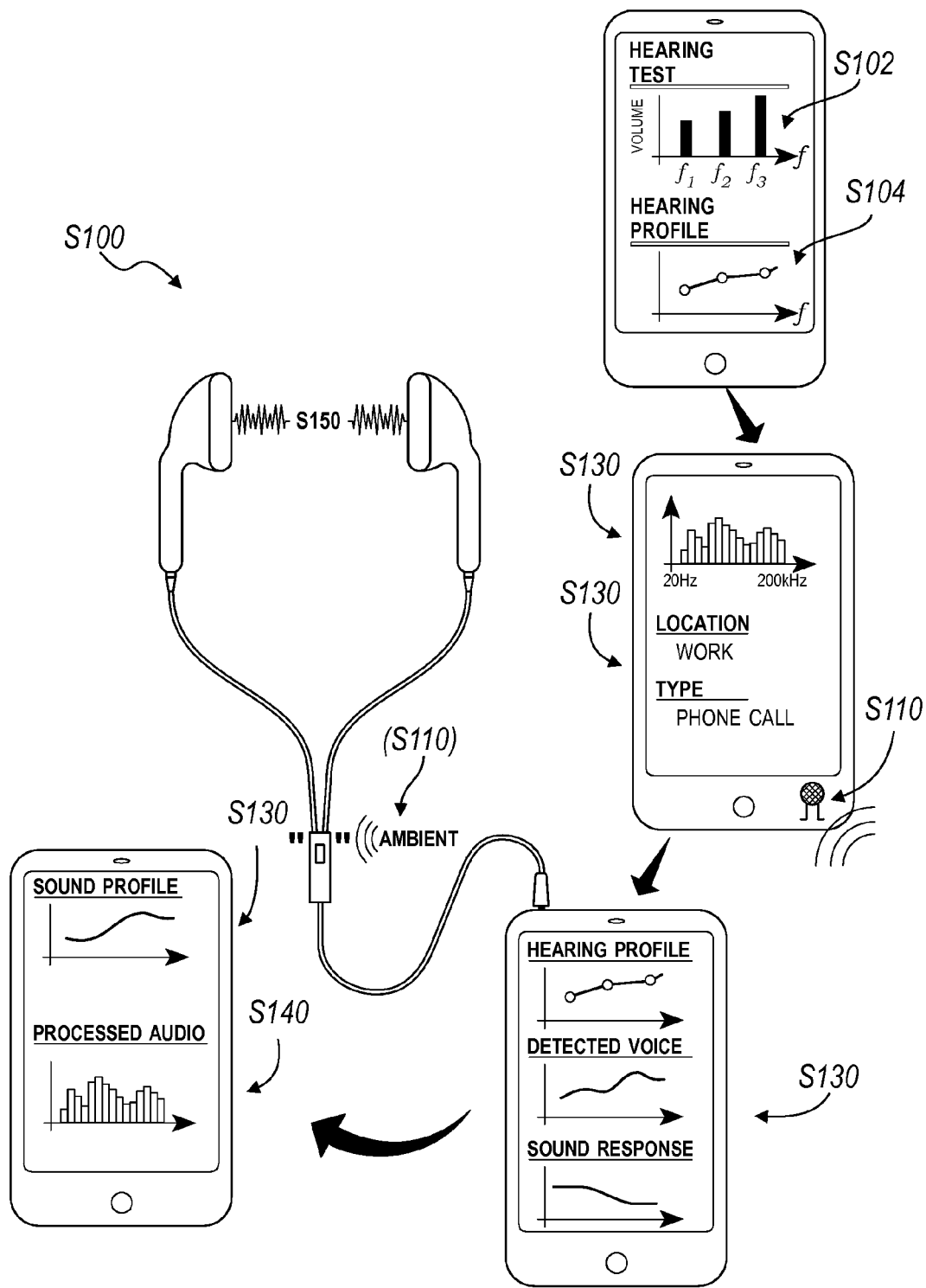
FIG. 1 is a flowchart representation of a method of one embodiment of the invention.

As shown in FIG. 1, a method for augmenting sound includes: at a mobile computing device and a connected audio output device, outputting a tone in a hearing test in Block S102; based on a response to the tone entered by a user, generating a hearing profile for the user and corresponding to the mobile computing device and the audio output device in Block S104; receiving an audio signal in Block S110; qualifying the audio signal as a particular audio type from a set of audio types in Block S120; selecting, from a set of sound profiles, a particular sound profile corresponding to the particular audio type in Block S130; at the mobile computing device, transforming the audio signal into a processed audio signal according to the particular sound profile and the hearing profile of the user in Block S140; and outputting the processed audio signal at the connected audio output device in Block S150.

Figure 3:
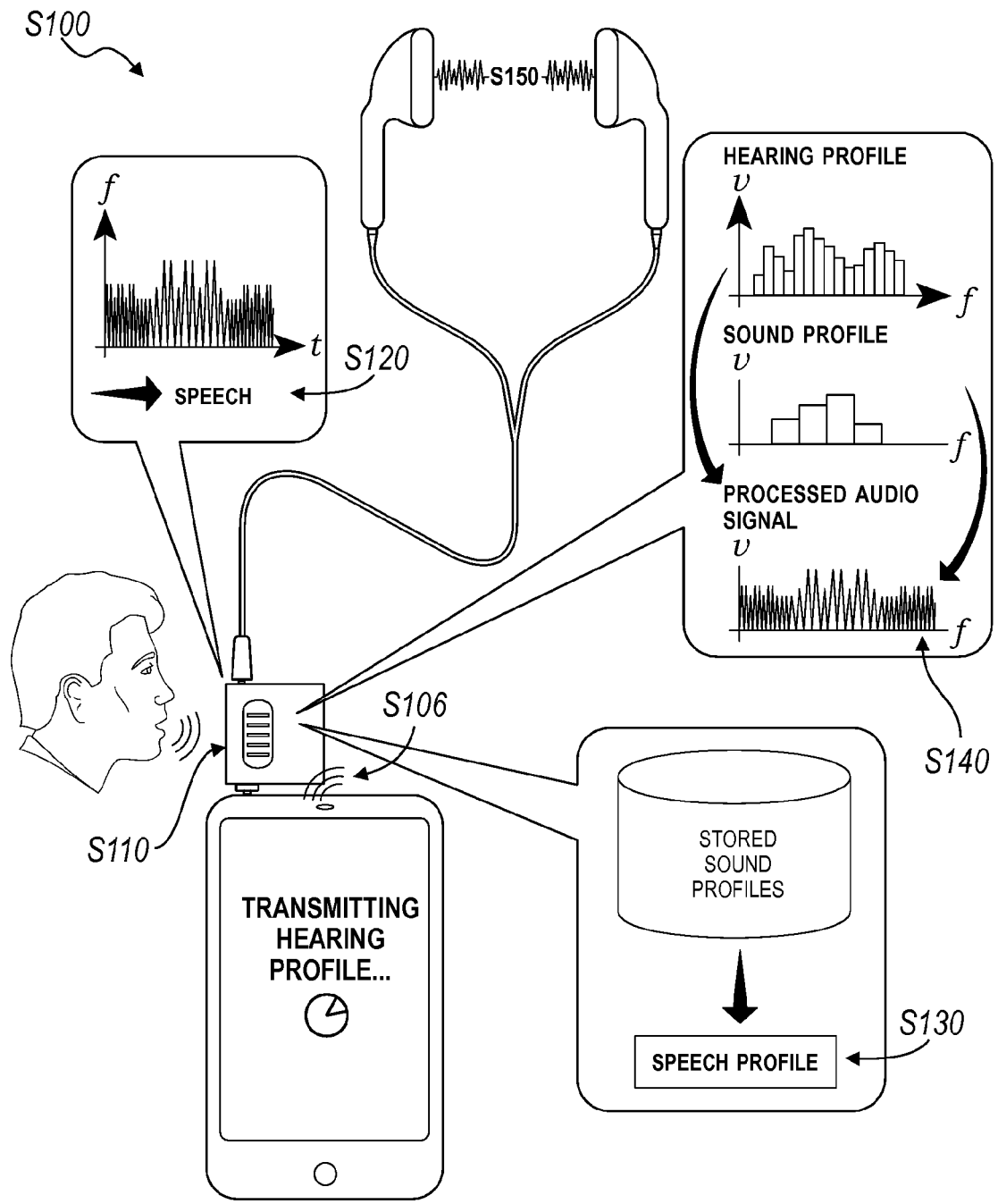
FIG. 3 is a flowchart representation in accordance with one variation of the method.

As shown in FIG. 3, one variation of the method S100 for augmenting sound includes: at an audio device, receiving a hearing profile from a mobile computing device in Block S106, the hearing profile corresponding to a user and generated on the mobile computing device; receiving an audio signal from the mobile computing device in Block S110; qualifying the audio signal as a particular audio type from a set of audio types in Block S120; selecting, from a set of sound profiles, a particular sound profile corresponding to the particular audio type in Block S130; transforming the audio signal into a processed audio signal according to the particular sound profile and the hearing profile of the user in Block S140; and substituting the audio signal for the processed audio signal at an output of the audio device in Block S150.

Generally, the method S100 functions to process (e.g., manipulate, change) an audio signal substantially in real-time according to a known hearing ability of a user and a sound profile specific to a characteristic, type, and/or origin of the audio signal, thereby dynamically adapting an output of an audio device specifically for the user across various listening scenarios. The method S100 can further process the audio signal according to an audio output profile of the audio device and/or a (mobile) computing device employed by the user and/or real-time factors that affect sound perception, such as location, acoustics of a room, time of day, activity or behavior of a user, a demographic of the user, etc. The method S100 can thus output an augmented audio signal substantially in real-time and tailored to an immediate hearing need of the user.

Once a hearing profile for the user is generated from a hearing test, the method S100 collects an audio signal in real time, qualifies the audio signal to determine a type or component of sound in the audio signal, selects a sound profile based on the type of audio signal (and/or various user-, location-, and/or device-related variables), and outputs an augmented audio signal based on the sound profile, the original audio signal, and the user's hearing profile in order to augment the user's perception of (details of) the audio signal. In particular, the method S100 can adjust the augmented audio output according to a type of audio signal and/or a current setting, behavior, action, and/or need of the user by selecting a sound profile, from a set of available sound profiles, most closely matched to the current audio signal type, setting, behavior, action, and/or need of the user and/or by adjusting a sound profile to substantially conform to the current audio type, setting, behavior, action, and/or need of the user. For example, the method S100 can process live sound, such as recorded through a microphone in the user's mobile computing device (e.g., smartphone, tablet) or transmitted to the users mobile computing device in a phone or video-conferencing call. The method S100 can additionally or alternatively process prerecorded audio files, such as local or streamed digital music files (e.g., MP3) or audio components of digital video files. However, the method S100 can be applied to any other real-time audio, prerecorded audio, streaming audio, or other digital or analog audio signal.

The method S100 can therefore be implemented in various settings, such as to aid the user in a face-to-face conversation with a single person or a small group of people in a closed room, to aid the user in a face-to-face conversation with multiple people in a crowded and/or boisterous space (e.g., while at dinner in a crowded restaurant), to aid the user in hearing a speech or lecture in an auditorium, or to aid the user in holding a phone conversation with a person in a quiet room or while walking down a busy street on a windy day. In further examples, the method S100 can to aid the user in hearing audio broadcast from a television, to aid the user in hearing higher-quality sound while attending a concert, opera, symphony, or other performance, or to augment the user's listening experience while playing music through headphone connected to an MP3 player, smartphone, etc. However, the method S100 can be applicable to any other scenario to augment the user's hearing and/or sound experience.

The method S100 can be implemented by one or more computer systems, such as a cloud-based computer system (e.g., Amazon EC3), a mainframe computer system, a grid-computer system, or any other suitable computer system. In one example implementation, the method S100 is implemented by a native application executing on a mobile computing device, such as a smartphone or tablet. For example, a smartphone (i.e., mobile computing device) can implement the method S100 in the form of a native hearing augmentation application (or "app") that generates a hearing profile of the user locally with a hearing test, receives local sounds through a microphone incorporated in the smartphone or in a headset or headphones worn by the user, adjusts the received sounds according to the user's hearing profile and the type of audio signal, and outputs the processed audio signal through the headset or headphones. In another example implementation, the method S100 is implemented through software executing on embedded circuitry (e.g., a processor or microcontroller) incorporated into an audio device, such as a standalone speaker, a home or car stereo system, a headset, or a set of headphones. In yet another example implementation, Blocks of the method S100 are implemented by a remote server in cooperation with a native application executing on a mobile computing device. In another example implementation, Blocks of the method S100 are implemented on a peripheral device arranged between an audio output of the user's mobile computing device (e.g., smartphone, tablet) and an input of an audio device (e.g., headset, set of headphones) such that the peripheral device processes an audio signal output from the mobile computing device and passes the processed audio signal to the connected audio device. The computer system can also incorporate a user interface through which the user can input responses to musical signals, review a hearing profile, enter demographic or other personal information, upload music or audio files, or enter, access, or review any other data or information. The use interface can be accessible through a web browser or through a native application executing on a (mobile) computing device, such as a laptop computer, a desktop computer, a tablet, a smartphone, a personal data assistant (PDA), a personal music player, etc. Generally, the audio device can include any device that outputs sound, such as a pair of headphones, a speaker, or a mobile phone. The computing device can include any device that processes a digital signal, such as a headset incorporating a microprocessor, a smartphone, or a tablet. However, the audio device, the peripheral device, and/or the computing device can be any other suitable type of device and can be discrete and/or physically coextensive (i.e., embodied in the same device).

In the implementation in which Blocks of the method S100 execute on a mobile computing device, the mobile computing device can execute Blocks S102 and S104 to test the user's hearing and to generate a hearing profile for the user accordingly. In particular, the method S100 can implement Blocks S102 and S104 to generate the user's hearing profile locally on the user's mobile computing device and/or the connected audio device such that an audio output profile of the mobile computing device and/or an audio output profile of a connected audio device are inherent in the hearing profile. Thus, when the audio signal is subsequently processed at the mobile computing device according to the hearing profile, the processed audio signal can compensate for the audio output profile of the mobile computing device and/or the audio output profile of the connected audio device, as these are inherent in the user's hearing profile. Thus, by generating the user's hearing profile locally, the method S100 can output a processed audio signal to augment the user's listening experience without identifying or accessing specific output profiles for the mobile computing device and/or for the audio device.

Similarly, in the implementation in which Blocks of the method S100 execute on a peripheral device (or locally on an audio device) connected to a mobile computing device, the peripheral device (or the connected audio device) can execute Block S106 to download the user's hearing profile from the mobile computing device. In this implementation, the mobile computing device can execute a method or technique like that of Blocks S102 and S106 to generate a hearing profile for the user and specific to the mobile computing device, the peripheral device, and/or the connected audio device, and the peripheral device (or the connected audio device) can thus download the hearing profile from the mobile computing device once the hearing profile is complete and available from the mobile computing device. Thus, in these implementations, the method S100 can generate the processed audio signal that inherently compensates for audio output profiles unique to the mobile computing device, the peripheral device, and/or the connected audio device by implementing a user hearing profile generated locally and specific to the combination mobile computing device, peripheral device, and/or connected audio device.

2. Hearing Profile

Block S102 of the method S100 recites, at a mobile computing device and a connected audio output device, outputting a tone in a hearing test. Block S104 of the method S100 further recites, based on a response to the tone entered by a user, generating a hearing profile for the user and corresponding to the mobile computing device and the audio output device. Generally, Blocks S102 and S104 of the method S100 implement an abbreviated (i.e., shortened) hearing test locally on the user's mobile computing device to generate a hearing profile specific to the mobile computing device (and the connected audio device) for the user.

Figure 5:
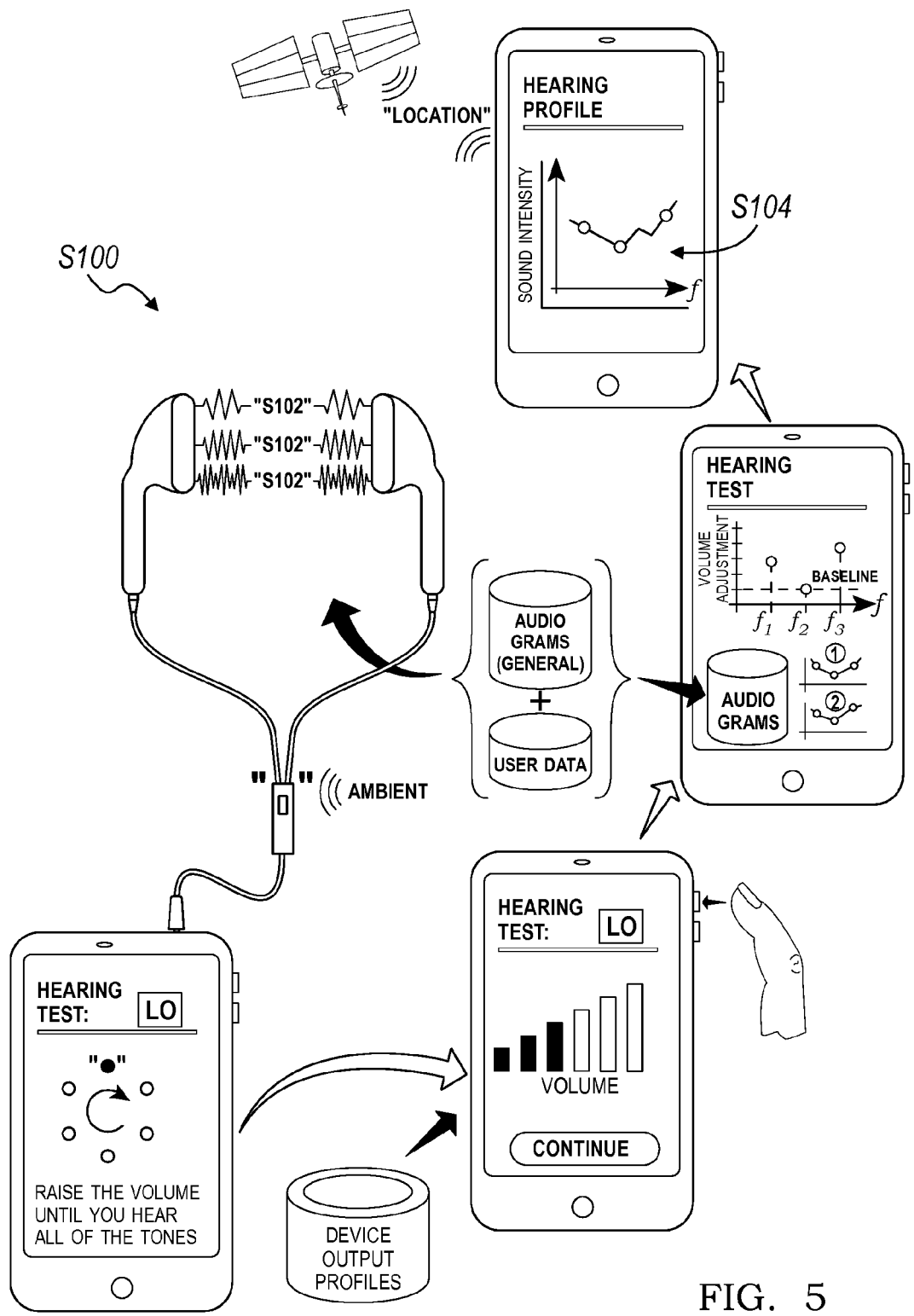
FIG. 5 is a flowchart representation in accordance with one variation of the method.

In one implementation, Blocks S102 and S104 cooperate to: output a first audible tone including a first frequency; record a first volume adjustment for the first audible tone by the user; output a second audible tone including a second frequency; record a second volume adjustment for the second audible tone by the user; select a particular hearing model from a set of hearing models based on a difference between the first volume adjustment and the second volume adjustment, each hearing model in the set of hearing models including a hearing test result corresponding to a previous patient; and generate the hearing profile for the user based on the particular hearing model result, as shown in FIG. 5.

In this implementation, Blocks S102 and S104 can generate a hearing profile that characterizes a user's hearing ability by testing the user's ability to hear a select subset of frequencies in the audible range, selecting a particular hearing test result from another user (or patient) who exhibits substantially similar hearing abilities at the select subset of frequencies, and applying data from the particular hearing test result to the user to fill in gaps in the hearing test at untested frequencies. In particular, Block S104 can collect a limited amount of hearing ability data from a user within a limited period of time (e.g., thirty seconds), characterize the limited amount of user hearing data, and "flesh out" or complete an image of the user's hearing ability across (at least a portion of) the audible range by applying preexisting hearing ability data from one or more other users to the user based on the characterization of the limited amount of hearing data from the user. For example, Block S104 can match volume adjustments entered by the user across two or more frequencies (output in Block S102) to hearing abilities at similar frequencies captured in an audiogram of a previous patient and then apply the audiogram of the previous patient to the user to estimate or predict the user's hearing abilities at other frequencies in the audible range. In another example, Block S104 can transform volume adjustments entered by the user across two or more frequencies into a parametric hearing model to output a synthetic audiogram for the user, wherein the parametric hearing model is generated from a series of audiograms of various other patients such that the synthetic audiogram specific to the user is a composite of multiple audiograms of other patients. However, Blocks S102 and S104 can apply hearing data from other patients to the user in any other way to estimate or predict a hearing ability of the user across an audible range given a limited amount of user hearing data captured in a limited amount of time (e.g., less time than required to capture a full audiogram). Furthermore, Blocks S102 and S104 can implement any other method or technique to generate a hearing profile for the user, such as described in U.S. Provisional Application No. 61/763,163, filed on 11 Feb. 2013, U.S. Provisional Application No. 61/831,796, filed on 6 Jun. 2013, U.S. Provisional Application No. 61/867,436, filed on 19 Aug. 2013, and U.S. Provisional Application No. 61/880,367, filed on 20 Sep. 2013, and U.S. patent application Ser. No. 14/148,034 filed on 11 Feb. 2014, all of which are incorporated in their entireties by this reference.

Thus, because Block S102 outputs one or more tones of a hearing test through the mobile computing device, the peripheral device, and/or the connected audio device, and because Block S104 generates the user's hearing profile locally on the mobile computing device based on audio output adjustments made by the user in response to the one or more tones, an audio signal subsequently processed according to the hearing profile in Block S140 can compensate for the audio output profile(s) of the mobile computing device, the peripheral device, and/or the connected audio device, as these audio output profiles are inherently accommodated in the hearing profile (i.e., the hearing profile is generated based on user responses to tones output in Block S102, which are subject to the audio output profiles of the mobile computing device, the peripheral device, and/or the connected audio device).

Once the hearing profile for the user is generated, Block S104 can further associate the hearing profile with an identifier of the mobile computing device and an identifier of the connected audio output device. For example, Block S104 can retrieve a unique serial number of the mobile computing device from a memory within the mobile computing device and then assign this unique serial number to the user's hearing profile. In this example, Block S104 can also prompt the user to enter a type (e.g., make and model), a serial number, or a SKU number, etc. of the connected audio device (e.g., a headset, a pair of headphones, a speaker) into a native hearing augmentation application executing on the mobile computing device, and Block S104 can then assign information entered by the user to the hearing profile. Alternatively, Block S104 can prompt the user to scan a barcode on packaging of the audio device or capture a picture of the audio device, and Block S104 can implement object or character recognition to identify the audio device and to then associate the audio device with the hearing profile accordingly. Yet alternatively, Block S104 can prompt the user to select an image displayed on the mobile computing device and corresponding to the audio device or to select the audio device from a drop-down menu.

Block S104 can also communicate directly with the audio device to retrieve an identifier of the audio device. For example, Block S104 can retrieve a unique Bluetooth ID or Wi-Fi ID from a wireless-enabled audio device and then assign this unique ID to the hearing profile. In this implementation, of the method S100 in which the audio signal is routed from the mobile computing device into the peripheral device and then into the connected audio device, Block S104 can implement similar functionality to detect, retrieve, and/or receive identification information for the peripheral device.

Block S104 can then store the hearing profile with one or more device-related assignments locally on the mobile computing device, and subsequent Blocks of the method S100 can retrieve and apply the stored hearing profile when one or more connected devices are matched to the hearing profile. For example, Block S104 can generate multiple hearing profiles, each specific to the mobile computing device with one or more other connected devices (e.g., various headphones, headsets, peripheral devices, etc.), and subsequent Blocks of the method S100 can selectively implement the hearing profiles according to detected and/or confirmed connected devices. Additionally or alternatively, Block S104 can store the hearing profile remotely, such as within an account assigned to the user and stored on a remote server. For example, Block S104 can store the hearing profile in the user's account with multiple other hearing profiles, wherein each hearing profile in the set is associated with different devices and/or a different combination of devices (e.g., mobile computing device, headset, set of headphones, peripheral device, etc.), and subsequent Blocks of the method S100 can selectively download and implement hearing profiles stored with the user's account according to detected or selected devices routing and/or outputting the audio signal. However, Blocks S102 and S104 can function in any other way to generate, tag, and store one or more hearing profiles for the user and one or more combinations of mobile computing devices, peripheral devices, and/or connected audio devices.

As shown in FIG. 3, one variation of the method S100 includes Block S106, which recites, at an audio device, receiving a hearing profile from a mobile computing device in Block S106, the hearing profile corresponding to a user and generated on the mobile computing device. In this variation of the method S100 in which one or more of Blocks S110, S120, S130, S140, and/or S150 execute on a peripheral device, the peripheral device (e.g., an audio processing unit arranged between an audio output of the mobile computing device and an audio input of a set of headphones) can implement Block S106 to retrieve a hearing profile from the mobile computing device. For example, Block S106 can include wirelessly downloading a hearing profile from the mobile computing device, such as over a Wi-Fi or Bluetooth connection. Alternatively, Bock S106 can receive the hearing profile over a wired connection, such as over an audio jack connection between the mobile computing device and the peripheral device. However, Block S106 can function in any other way to retrieve a hearing profile from the mobile computing device for application in subsequent Blocks of the method S100.

Similarly, in a variation of the method S100 in which one or more of Blocks S110, S120, S130, S140, and/or S150 execute on a connected audio device (e.g., a headset), the connected audio device can similarly implement Block S106 to retrieve a hearing profile from the mobile computing device, such as over a wired or wireless connection.

3. Audio Signal

As shown in FIG. 1, Block S110 of the method S100 recites receiving an audio signal. Generally, Block S110 functions to handle audio signals from one or more sources, including live sound (e.g., captured at a microphone integrated into the mobile computing device, a headset, or a set of headphones or transmitted to the mobile computing device from an external device) and prerecorded audio, such as from music or film in playback on the mobile computing device or played near the mobile computing device.

In one implementation, Block S110 captures or receives live sound through a microphone arranged within or in communication with the user's mobile computing device. In one example, Block S110 captures sound through a microphone integrated into the mobile computing device. In another mobile computing device, Block S110 receives sound through a microphone incorporated into the connected audio device carried or worn or carried by the users, such as the a headset or a set of headphones. In this example, Block S110 can receive the audio signal via wired or short-range wireless communication, such as over Bluetooth or Wi-Fi. In another example, Block S110 receives sound through a microphone incorporated into a device worn or carried by another user, such as a cellular phone or a tablet carried by a second user during a phone call, video conference call, or similar communication with the user. In this example, Block S110 can receive the audio signal from the external device via short- or long-range wireless communication, such as over Bluetooth, Wi-Fi, or cellular communication protocol, or over a landline or Internet connection. In particular, in this example, Block S110 can identify an audio output from a native phone or video conferencing application executing on the user's mobile computing device. In another example, Block S110 receives the audio signal recorded through and transmitted from a standalone microphone arranged within a space occupied by the user, such as an auditorium or an amphitheatre. Thus, Block S110 can interface with one or more microphones in the user's mobile computing device, an audio and/or peripheral device connected to the user's mobile computing device, an external device, etc. to collect a live sound or local sound in playback in the form of an audio signal.

Block S110 can also receive pre-recorded audio, such as from a sound file (e.g., an MP3 audio file) stored locally on the mobile computing device during playback or streamed to the mobile computing device, such as over the Internet from an online music or video service. For example, Block S110 can identify an audio output from a native music or video application executing on the user's mobile computing device.

Block S110 can further receive multiple (live) audio signals substantially simultaneously. For example, Block S110 can collect a first audio signal of the user's voice from a microphone incorporated into a headset worn by the user, a second audio signal of the voice of a second user from a microphone incorporated into a second smartphone used by the second user, and a third audio signal of ambient noise proximal the user from a microphone incorporated into the user's smartphone during a phone conversation between the user and the second user. In another example, as shown in FIG. 1, Block S110 can collect a first audio signal from a microphone incorporated into a set of headphones worn by the user and a second audio signal of the user's voice from a microphone incorporated into the user's smartphone, thereby enabling the method S100 to generate a substantially three-dimensional soundscape (e.g., sound image) of the space occupied by the user.

In the variation in which the peripheral device executes various Blocks of the method S100, the peripheral device can capture the audio signal through a microphone incorporated into the peripheral device. Additionally or alternatively, the peripheral device can receive the audio signal from the user's mobile computing device, such as over a wired or wireless connection with the mobile computing device. For example, Block S110 can receive the audio signal over an audio output jack within the mobile computing device. However, Block S110 can function in any other way to receive or collect one or more audio signals.

Block S120 of the method S100 recites qualifying the audio signal as a particular audio type from a set of audio types. Generally, Block S120 functions to identify a type of the audio signal. For example, Block S120 can select a particular audio type—from a set of audio types including music, speech, and ambient noise—and assign the selected audio type to the audio signal. In this example, Block S120 can also identify the audio signal as an audio component of phone call between the user's mobile computing device and a secondary device of another user.

Figure 2:
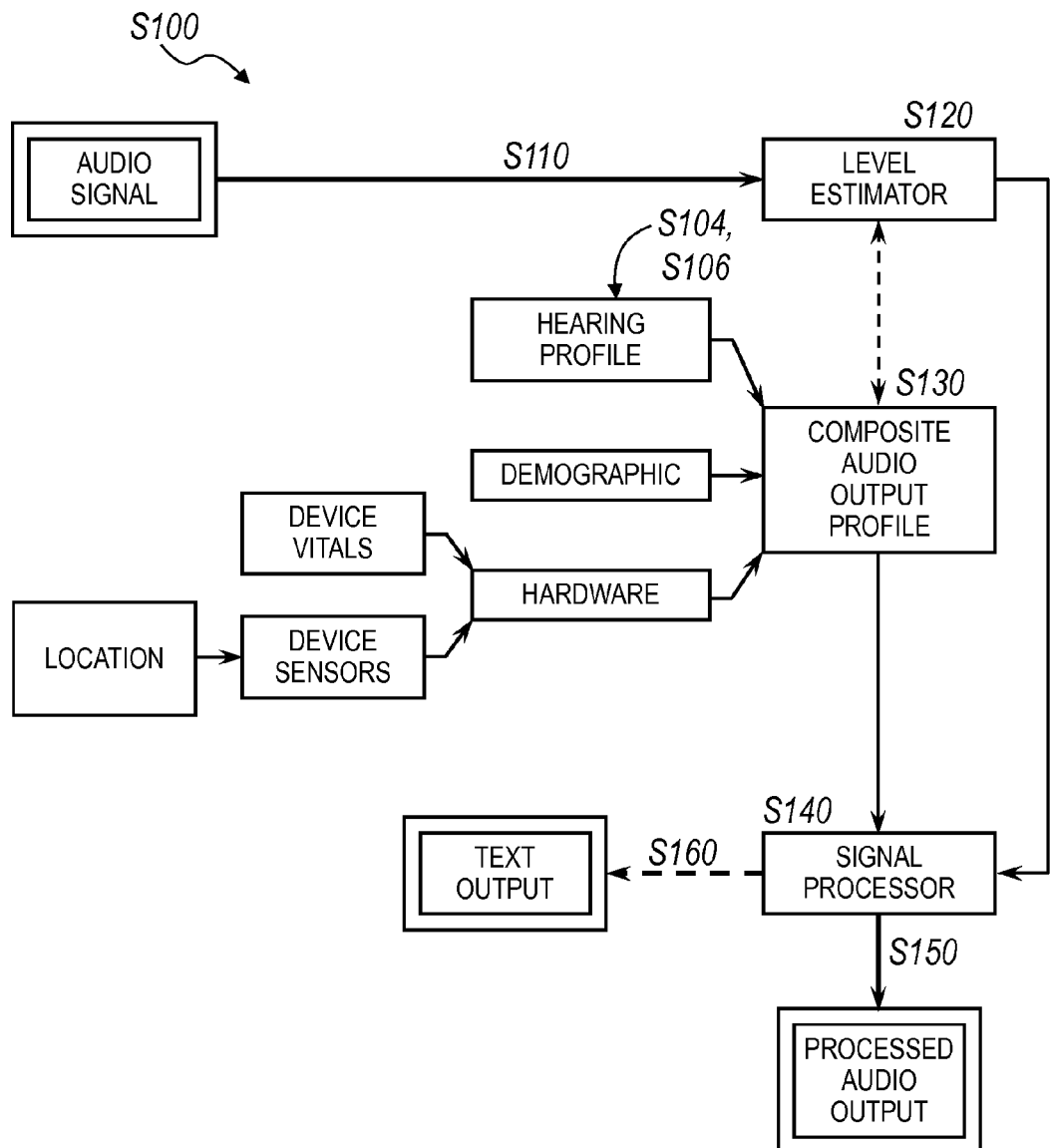
FIG. 2 is a flowchart representation in accordance with one variation of the method.

In one implementation, Block S120 applies a level estimator and/or other processing algorithm to determine a type of sound in the audio signal, as shown in FIG. 2. For example, Block S120 can determine the audio signal to include music, speech, or machine noise. In one example implementation, Block S120 evaluates the audio signal to identify a key characteristic of the audio signal, such as volume, type of sound (e.g., speech, music, white noise), proximity or origin of sound, and/or any other factor that informs selection of a processing algorithm to apply to the audio signal to augment the user's consumption of the audio signal. For example, Block S120 can apply a Weighted Overlap-Add (WOLA) filter bank to decompose the audio signal into discrete frequency bands, wherein a substantially continuous tone or set of tones without substantial variation in tonal quality or amplitude is associated with machine noise, wherein interrupted tones in the range of 300 Hz to 3400 Hz is identified as speech, and wherein continuous sound of varying amplitude across a varying range of frequencies is identified as music. In this example, Block S120 can qualify the audio signal to greater resolution, such as by identifying machine noise originating specifically from a computer cooling fan or from a car engine.

In another example, Block S120 can identify a man's voice, a woman's voice, a child's voice, and/or the user's voice in the audio signal and, based on fluctuations in and/or reverberations of an identified voice, characterize the voice as speaking, whispering, shouting, singing, and/or humming, etc. Then, in this example, Block S120 can qualify the audio signal containing the voice(s) as local conversation, a phone call, music, or ambient noise, etc. Block S120 can further qualify the audio signal based on timing of one voice in the audio signal relative to another voice in the audio signal. For example, if Block S120 identifies two separate voices of similar audible level and that occur substantially asynchronously in the audio signal, Block S120 can characterize the audio signal as a live phone call between the user and another individual, and, if Block S120 identifies two separate voices at significantly different audible levels occurring substantially asynchronously in the audio signal, Block S120 can characterize the audio signal as a live local conversation between the user and another individual.

Block S120 can additionally or alternatively estimate the origin of a particular sound in the audio signal. Based on origins of sounds in the audio signal, Block S120 can assign priority levels to one or more sources of the sound in the audio signal. In the implementation in which Block S110 collects the audio signal from a single microphone, Block S120 can analyze the audio signal, identify echoes in the audio signal, and generate a sound map of the space occupied by the user based on the identified echoes in the audio signal. Similarly, in the implementation in which Block S110 collects audio signals from multiple microphones, Block S120 can combine the multiple audio signals into a three-dimensional sound image of the space occupied by the user. Block S120 can also analyze volume, frequency, and/or frequency-response data of the space occupied by the microphone (e.g., the mobile computing device and/or the audio device) to identify sounds originating near the microphone (and therefore near the user) and sounds originating substantially removed from the microphone (and therefore removed from the user). In an example in which the user is in a crowded restaurant, Block S120 can apply a highest priority to sounds originating nearest and in front of the user, a moderate priority to sounds originating nearest and behind the user, and a lowest priority to sounds originating at a distance greater than eight feet from the user. Similarly, in an example in which the user is in an auditorium, Block S120 can apply a highest priority to sounds originating furthest and in front of the user, a moderate priority to sounds originating nearest and beside the user, and a lowest priority to sounds originating behind the user. In these examples, Block S130 can select or adjust a sound profile according to priorities set by Block S120, and Block S140 can apply a filter to the audio signal according to priorities set in Block S120. However, Block S120 can estimate and apply sound origin data in any other suitable way.

Block S120 can also implement voice detection, voice recognition, and/or other audio processing techniques to identify the voice in the audio signal. For example, Block S120 can assign priority to a voice that is determined to be particularly relevant to the user, such as a coworker who often speaks with the user, a person at a dining table with the user, or a speaker in an auditorium. In this example, the method S100 can filter out sounds and/or voices not prioritized in Block S120 such that the user can hear and focus on sounds most relevant to him. In another example, Block S120 can recognize and flag the user's voice. In this example, the method S100 can further filter out the user's voice, thus aiding the user in audibly discerning other sounds while talking, singing, etc. without substantially amplifying his own voice. Block S120 can further detect changes in the audio signal to trigger changes to sound profile, such as in response to a switch from detected speech to detected music or song in the audio signal.

Block S120 can additionally or alternatively quantify the volume of the audio signal, such as by extracting the amplitude (i.e., volume) of components of the audio signal. From these data, Block S140 can remove or filter out—from the audio signal—sounds below a threshold volume level. For example, Block S140 can filter out a low hum of a refrigerator or low-volume cyclic insect sound. In another example, Block S140 can filter out or attenuate sounds above a threshold volume, such as to implement hearing protection functionality.

Block S120 can additionally or alternatively qualify the audio signal as a particular audio type based on a source of the audio signal. For example, when implemented within a native hearing augmentation application executing on the user's mobile computing device, for Block S120 can qualify the audio signal as a speech in a phone call when a native phone application is active on the mobile computing device, as music when a native music playback application is active on the mobile computing device, and as an audio component of a video when a native video application is active on the mobile computing device. In this example, Block S120 can also analyze a filename for a music track or video in playback on the mobile computing device to identify a type of music represented in the track (e.g., rock, punk, classical, reggae, or R&B, etc.) or a type of audio represented in the video (e.g., music, speech, action noise, ambient noise, machine noise, etc.), respectively. Block S120 can also filter available audio types (from the set of audio types) based on a source of the audio signal. For example, when implemented on a peripheral device arranged between the user's mobile computing device and the connected audio device, Block S120 can filter the set of audio types in the set down to live audio for audio signal received from a microphone within the peripheral device and the connected audio device (e.g., a setoff headphones) and prioritize prerecorded audio signal classification for audio signals received from the mobile computing device.

However, Block S120 can function in any other way to assign an audio type to an audio signal received or captured in Block S110.

4. Sound Profile

As shown in FIG. 1, Block S130 of the method S100 recites selecting, from a set of sound profiles, a particular sound profile corresponding to the particular audio type. Generally, Block S130 functions to select a sound profile specific to the audio type, which is subsequently implemented in Block S140 in conjunction with the user's hearing profile to modify the audio signal in anticipation of the user's particular hearing needs for the particular audio type. For example, Block S130 can retrieve the particular sound profile from a set of sound profiles stored locally on the user's mobile computing device or on the peripheral device based on an the audio type identified in Block S120. Alternatively, Block S130 can download the sound profile from a remote server and locally store the sound profile independently or with a limited set of common-use sound profiles on the user's mobile computing device or on the peripheral device.

In one implementation, sound profiles in the set of sound profiles are static or 'fixed' across all users over time. Alternatively, when a new account is created for new user, a standardized sound profile (i.e., common across multiple new users) can be assigned to the user, and the sound profile can be subsequently modified for the user—independent adjustments to the same standard sound profile for other users—over time as the user supplies feedback during application of the sound profile to various audio signals. For example, in one variation of the method, Block S130 detect an audio type of a sound output from the audio device, receives an audio output adjustment from the user, generates a sound profile for the audio type based on the audio output adjustment from the user, and stores the sound profile with the set of sound profiles. For example, in this variation, Block S130 can adjust a volume setting, an equalizer (EQ) setting, and/or another user preference within the sound profile for a particular audio type as the user makes adjustments to a processed audio signal of an identified type over time. Additionally or alternatively, Block S130 can populate the set of audio profiles by generating new audio profiles based on user audio adjustments made during identified use scenarios classified as new or more-specific audio types. For example, Block S130 can detect an ambient noise condition, receive a volume adjustment from the user during output of a sound from the audio device, and then generate a sound profile for a new audio type associated with the ambient noise condition based on the volume adjustment entered by the user. Block S120 can subsequently match an audio signal to the ambient noise condition, and Block S130 can retrieve the sound profile for the ambient noise condition accordingly.

Yet alternatively, Block S130 can select from the set of sound profiles that is populated over time from adjustments made by various users during various classified scenarios, and the sound profiles in the set can also be updates or modified over time based on adjustments made across various users. For example, Block S130 can generate and/or update sound profiles based on feedback from users of various demographics (e.g., age, gender, ethnicity, occupation, location, etc.) and then group feedback and corresponding updated sound profiles accordingly. In this example, Block S130 can thus select a particular sound profile—from the set of sound profiles—that is associated or 'tagged' with one or more demographics shared with the user.

Thus, as shown in FIG. 2, Block S130 can access one or more demographics of the user and apply the demographic(s) of the user to selection of the particular sound profile from the set. For example, Block S130 can extract an age, gender, location, ethnicity, and/or occupation of the user from a user profile stored within a social networking system linked to the native hearing augmentation application executing on the user's mobile computing device. Block S130 can subsequently select a particular sound profile previously elected by a second user of a demographic (e.g., an age, a gender, etc.) similar to one or more demographics of the user. Additionally or alternatively, Block S130 can identify a location of the user, such as by retrieving a current location of the user's mobile computing device from a Global Positioning System (GPS) sensor within the mobile computing device. In this implementation, Block S130 can subsequently select a particular sound profile—from the set of sound profiles—that corresponds to the particular audio type for a location type including the location of the user or that falls within a threshold range or distance of a particular location associated with the particular sound type.

In one implementation, Block S130 selects an sound profile, to be applied to the audio signal in Block S140, from a database of algorithms (e.g., fillers) unique to the user. In this implementation, the database of algorithms includes preset sound profiles selected, preferred, and/or developed by the user over time in conjunction with a native application, applet, or other software module, such as executing on the user's mobile computing device. The database of algorithms can therefore include an sound profile tailored by and/or specific to the user for one or more use scenarios. In another implementation, Block S130 selects the sound profile—to be applied to the audio signal in Block S140—from a database of algorithms shared across a set of users including the user. In this implementation, algorithms in the database can be static and preset, or the algorithms can be added and/or adjusted by one or more users in the set of users over time, such as to crowdsource creation and refinement of sound profile, such as for a particular user demographic, a particular hearing or sound preference, a particular location, a particular user habit, etc. Therefore, in this implementation, the user can be grouped with a set of users according to similar hearing or sound preferences, similar demographic(s), similar locations, similar habits, etc. However, Block S130 can select sound profile from any other one or more databases of algorithms in any other suitable way.

Additionally or alternatively, Block S130 can adjust a current or selected sound profile. For example, Block S130 can adjust a channel transformation of a current filter or gain applied to a particular channel to account for real-time changes in sound-related parameters. For example, for a selected sound profile particular to a certain restaurant, Block S130 can adjust a transformation specified by the sound profile as the restaurant becomes more crowded (and therefore more boisterous) and/or as the restaurant becomes less crowded (and therefore quieter). In another example, for a selected sound profile particular to the user's habitual weeknight reading, Block S130 can adjust a transformation specified by the sound profile to specify an overall decrease in total sound level as the user's typical bed time approaches. However, Block S130 can function in any other way to select and/or adjust the sound profile.

Block S130 can therefore select and/or adjust the sound profile dynamically according to any one or more of the user's hearing profile, the user's location, the user's demographic, a quality of audio-based hardware of one or more devices implementing the method S100 (e.g., the user's mobile computing device, the peripheral device, and/or the audio device), a vital quality of one or more devices implementing the method S100 (e.g., remaining battery life in the mobile computing device), a current time of day, and/or a detected user action, etc.

As shown in FIG. 3, Block S130 can implement the user's hearing profile (as described in U.S. Provisional Application No. 61/880,367, filed on 20 Sep. 2013 and incorporated herein by reference) to access quantitative and/or qualitative data pertaining to how well the users hears certain frequencies. Block S130 can also access hearing preferences of the user from the hearing profile, such as sensitivity to high frequency sounds. Based on the hearing profile, Block S130 can select and/or adjust the sound profile to complement the user's hearing needs and/or hearing preferences. For example, the hearing profile can indicate that the user has difficulty hearing sounds between 20 Hz and 120 Hz, which Block S130 can implement by selecting (or adjusting) the sound profile that increases the gain in the audio signal within the range of 20 Hz and 120 Hz. In another example, the hearing profile can indicate that the user prefers not to hear low-frequency machine noise while working but does prefer low-frequency machine noise (e.g., as white noise) while sleeping, and Block S130 can implement these preferences by selecting (or adjusting) a first sound profile that attenuates machine noise during the day and by selecting (or adjusting) a second sound profile that boosts machine noise at night.

As shown in FIG. 3, Block S130 can implement the user's location to select an sound profile particular to a certain setting, room, or space or to a certain type of setting, room, or space. In one implementation, Block S130 accesses GPS data, Wi-Fi data, cellular data, a user check-in, or recent user credit card data, etc. to determine or estimate the current location of the user. From these data, Block S130 can determine that the user is currently occupying a particular room or a particular space. In another implementation, Block S130 accesses data (e.g., GPS data and/or motion data from cellular phones carried by the other users) from other users proximal the user and estimates the type of space currently occupied by the user. For example, Block S130 can determine the user to be in a restaurant based on GPS data from other users that shows clusters of two to six users in the space, and Block S130 can further determine the crowdedness of the restaurant based on the density of other users in the space.

Based on the location of or the determined or estimated space occupied by the user, Block S130 can select (or adjust) the sound profile based on a sound response of the space. The sound response of the space can be estimated based on the size, shape, type, and/or occupancy, etc. of the space, or selected from a known sound response previously associated with the space. For example, the sound response of a workspace of the user can attenuate high frequency sounds and amplify low frequency sounds with minimal echo. Block S130 can thus identify the sound response of the space from a list of sound responses of spaces common to the user and select the sound profile accordingly. Block S130 can additionally or alternatively identify the sound response of the space from a database of sound responses generated by and shared across multiple users who frequent spaces common to the user. Block S130 can therefore implement machine learning and/or crowd-sourcing techniques to develop a sound response database of spaces or types of spaces.

Block S130 can also generate a sound profile of the space occupied by the user. For example, when the user enters the space, Block S130 can trigger multiple sequential audible clicks from a speaker within a smartphone carried by the user, record subsequent reverberation of the clicks through the space, and characterize the space according to the recorded reverberations, which can be correlated with sound travel and dissipation through the space and thus the size of, shape of, and/or materials within the space. Block S130 can then access the foregoing sound response when the user next enters the space. However, Block S130 can estimate how the room responds to sound in any other suitable way.

Once the location, space, and/or sound response of the room is identified, Block S130 can tailor the sound profile to the user's hearing needs and/or to preferences specified in the user's hearing profile.

As described above, Block S130 can also implement a demographic of the user to predict a hearing preference of the user and to then select or adjust the sound profile accordingly. In this implementation, Block S130 can access any one or more of the user's age, gender, marital or familial status, employment status, cultural background or ethnicity, etc. and estimate a hearing preference of the user based on preferences of other users of similar demographics. For example, Block S130 can interface with an online social network to automatically source user demographic data, as shown in FIG. 1. In one implementation, the user's hearing preference is applicable to one or more particular social settings or during some form of identifiable human interaction. For example, for the user who is over the age of fifty, Block S130 can determine, based on the user's age, that the user is likely to prefer amplification of sounds directly in front of him and attenuation of sounds behind him, and for the user who is under the age of thirty-five, Block S130 can determine, based on the user's age, that the user is likely to prefer balanced amplification of sounds around him. Similarly, for the user who lives alone or with only a spouse, Block S130 can determine, based on the living arrangement, that the user is likely to prefer amplification of sounds directly in front of him and attenuation of sounds behind him, and for the user who has a large family or lives with several people, Block S130 can determine, based on the living arrangement, that the user is likely to prefer balanced amplification of sounds around him. Alternatively, the hearing preference can be entered directly by the user, and Block S130 can select and/or adjust the sound profile according to the determined or entered user preference. However, Block S130 can apply the user's hearing preference in any other way.

As shown in FIG. 3, Block S130 can additionally or alternatively identify a particular person or persons with whom the user commonly interacts. In this implementation, Block S130 can apply priority to sounds, in the audio signal, associated with such person or persons. For example, Block S130 can interface with the online social network to identity a spouse, a parent, or a child of the user. In this example, Block S130 can identify the presence of the spouse, parent, or child proximal the user based on a mobile phone number sourced from the online social network and a GPS coordinate of a mobile phone associated with the mobile phone number. Block S130 can thus select and/or modify the sound profile accordingly, such as by selectively augmenting and/or prioritizing a voice of one or more the spouse, parent, and/or child when each is determined to be proximal the user.

As shown in FIG. 3, Block S130 can further leverage a second sound profile implemented by a second user proximal the user. For example, Block S130 can elect a second sound profile currently implemented for the second user as a baseline to select or adjust the sound profile for the user. The method S100 can also add components (e.g., frequencies) of the second audio signal from the second user to the audio signal, thereby augmenting the audio signal with audio data from a second source. For example, if the second user is seated in a prime listening location in a symphony hall and the user is seated in a back corner of the symphony hall (i.e., a less-than-optimal acoustic position), the method S100 can boost (or replace) the audio signal of the user with a second audio signal collected at a computing device and/or audio device arranged on or carried by the second user, thereby augmenting the user's listening experience with sound data from another user elsewhere in the audience substantially in real-time. In another example, for the second member who is seated near a third member at a conference table, wherein the user is substantially removed from the second and third members at the conference table, the method S100 can augment an audio signal collected at the user's computing device with a second audio signal and/or a third audio signal collected at computing devices at the second member and the third member, respectively, as each speaks, thereby enabling the user to hear the second and third members.

As shown in FIG. 3, Block S130 can also implement a current time and/or a current user action to select and/or adjust the sound profile. In one implementation, Block S130 tracks the user's habits over time and generate a schedule for the user accordingly. For example, Block S130 can determines that the user often (e.g., with at least 85% accuracy) is asleep between the hours of midnight and 6 am, wakes between 6:30 and 6: 45 am, eats breakfast with his roommate between 7:15 am and 7:30 am, commutes to work between 7:45 am and 8:30 am, works from 8:30 am until noon, etc. In this example, Block S130 can adjust the sound profile to attenuate high frequency noises between midnight and 6 am, boost-mid range noise between 6:30 and 6:45 am (so the user does not miss his alarm clock), amplify audible frequencies characteristic of the speech (or more specifically the roommate's voice) between 7:15 am and 7:30 am, attenuate low-frequency noise (e.g., road noise) between 7:45 am and 8:30 am, attenuate high-frequency noise between 8:30 am and noon while the user is at work, etc. Block can estimate a current action of the user based on time according to a schedule entered by the user, schedules common to the user's demographic, the roommate's schedule, a coworker's schedule, etc.

As shown in FIG. 3, Block S130 can additionally or alternatively estimate a current user action (and adjust the sound profile accordingly) based on motion data of the user, such as measured by an accelerometer and/or gyroscope incorporated into a mobile computing device (e.g., smartphone) carried by the user and implementing portions of the method S100. Block S130 can further apply local sound data and/or location data of the user to verify or further inform a current user action. In one example, Block S130 associates low detected user movement (e.g., below a threshold displacement within a period of time) and low sound levels around 8 pm with reading, and Block S130 can thus adjust the sound profile to attenuate substantially all sound at this time. In another example, Block S130 can associate little movement and lots of sound around 8 pm with watching television, and Block S130 can thus adjust the sound profile to amplify frequencies that the user does not hear well. In a further example, Block S130 can associate little movement and little sound around 10 am with working, and Block S130 can thus adjust the sound profile to attenuate higher-frequency sounds. In yet another example, Block S130 can associate lots of movement and a moderate sound level around 6 pm with working, and Block S130 can thus adjust the sound profile to attenuate frequencies associated with voices of (the user's) children.

Block S130 can also account for a sound or signal input profile of one or more microphones or amplifiers that record the audio signal, as well as a sound or signal output profile for amplifiers, speakers, and/or one or more devices implementing portions of the method S100. In this implementation, Block S130 can select and/or tailor the sound profile to account for how sound is altered when recorded and output to the user through various devices such that a particular quality of a particular sound type is heard by the user across various devices or combinations of devices.

Block S130 can further select and/or adjust the sound profile based on a vital of the computing device implementing a portion of the method S100. In one implementation, Block S130 accesses a battery level of the computing device and selects and/or adjusts the sound profile that extends the life of the device's battery if the battery level is below a predetermined threshold. For example, if the battery level is substantially low, Block S130 can select and/or adjust the sound profile that reduces processing power and/or audio power by selectively augment sound to give user only what is most necessary for the user to function.

By applying one or more of the foregoing techniques, Block S130 can select and/or adjust the sound profile that is particularly suitable for application to the audio signal for the user at a particular (i.e., current) time. For example, the sound profile can therefore be tailored and/or specific to music through headphones, watching a concert in a particular venue, talking on the phone with a phone to the ear in a crowded space, talking on the phone via speakerphone in a quiet room, conversing with friends at a table in a restaurant, working at a desk in a quiet office, hiking up a mountain, watching television at home, watching a sporting event in a bar, during band practice, while driving, or in any other scenario or setting classified in Block S120. Block S130 can also adjust multiple sound profiles simultaneously and thus enable the user to elect or switch between sound profiles manually and substantially on the fly.

Block S130 can repeat continuously or cyclically (e.g., at a specified time interval) to adjust the sound profile substantially in real-time. For example, Block S130 can cycle at a rate of 10 Hz to continuously detect the user's current action, location, etc. and to update the sound profile accordingly, such as as the user moves between rooms within a building or as a restaurant fills and then empties over time. However, Block S130 can function in any other way to select and/or adjust the sound profile that is applied to the audio signal in Block S140.

5. Audio Signal Transformation

As shown in FIG. 1, Block S140 of the method S100 recites, at the mobile computing device, transforming the audio signal into a processed audio signal according to the particular sound profile and the hearing profile of the user, as shown in FIGS. 1, 2, and 3. Generally, Block S140 functions to apply the sound profile an the user's hearing profile to the audio signal, thereby modifying the audio signal to accommodate both the user's hearing ability (as defined in the user's hearing profile) and the user's current audio scenario (as defined by the selected sound profile). In particular, Block S140 can attenuate, amplify, and/or leave unchanged one or more channels (i.e., frequency bands) of the audio signal according to the combination of the hearing profiles and the selected sound profile. Block S140 can thus process the audio signal according to the hearing profile and the sound profile to darken, brighten, warm, or cool the audio signal, to target amplification of a certain voice or group of voices in the audio signal, to balance the audio signal for a certain frequency response of a room, auditorium, or other space occupied by the user, or to boost or augment the audio signal with audio data from a third party (e.g., second user), etc. In one example, Block S140 applies—to the to the audio signal—a first equalizer setting specified by the particular sound profile and a second equalizer setting specified by the user's hearing profile. In this example, Block S140 can also apply different weights to the hearing profile and the sound profile in processing the audio signal. Alternatively, the sound profile can define an algorithm for modifying the hearing profile (or vice versa), and Block S140 can apply the sound profile to the hearing profile to adjust the hearing profile for the classified audio type of the audio signal before processing the audio signal according to the adjusted hearing profile. In another example, during a phone call hosted by the user's mobile computing device, Block S140 attenuates a portion of a first audio signal corresponding to a voice of the user and recorded at the user's mobile computing device, amplifies a portion of a second audio signal received from another device (of another user) according to the particular sound profile, and combines the processed first audio signal with the processed second audio signal. In yet another example, a transformation of the audio signal specified in a sound profile can define compression and/or gain parameters for one or more frequencies within the audio signal, and Block S140 can decompose the audio signal into various frequency bands (i.e., frequency channels) and apply a particular transformation specified in the sound profile to each corresponding frequency band.

In one implementation, Block S140 also retrieves the user's hearing profile for subsequent application to the audio signal. For example, Block S140 can collect an identifier of the user's mobile computing device, the peripheral device, and/or the connected audio device and then retrieve the hearing profile from the user's hearing account (stored in a remote database or locally on the mobile computing device or on the peripheral device) by matching identifiers tagged to the hearing profile to the identifiers collected from the mobile computing device, the peripheral device, and/or the connected audio device. Block S140 can thus select a user hearing profile—from a set of available user hearing profiles—specific to a current combination of mobile computing device, peripheral device, and/or connected audio engaged by the user.

In one implementation, Block S140 aggregates the user's hearing profile, the sound profile, and local and/or environmental conditions into a composite output profile and processes the audio signal according to the composite output profile. In this implementation, the method S100 can dynamically adjust the composite output profile according to a changing audio signal and/or a changing local or environmental condition based on feedback and use data supplied by other users. In particular, Block S140 can dynamically modify a transformation of one or more frequencies within the sound signal as defined by one or both of the hearing profile and the sound profile. For example, Block S140 can select, set, and/or adjust parameters of a sound and/or hearing profile applied to the audio signal dynamically and over time based on a change in user location, ambient noise level, detected audio type, etc. detected in Block S130.

In the foregoing implementation, Block S130 can collect environmental data from various users over time, store these data in a database, identify changes in environmental conditions within the data, and pair or 'tag' identified environmental changes with user feedback. In one example, Block S130 identifies an increase in ambient noise in a datum collected from a first user and tags this datum with a manual increase in volume of output audio entered by the first user. In another example, Block S130 collects a local sound response through a microphone within a smartphone associated with a second user, identifies a change in the local sound response (e.g., as a user walks into a different room or as a room occupied by the second user fills with additional people), and tags the change in local sound response with a corresponding manual EQ setting change entered by the second user. Block S130 can thus collect, analyze, and store such events and tag these events with feedback from corresponding users. Block S140 can subsequently modify the sound profile, the hearing profile, and/or the composite output profile according to detected events and corresponding tags, such as in real-time as new events are detected and matched to past events paired with user feedback.

Block S140 can further implement the hearing and sound profiles to enable various other functionalities, such as hearing protection, or to aid a particular user action, such as talking on the phone, driving a car, or conversing in a meeting. However, Block S140 can function in any other way to process the audio signal according to the selected sound profile.

6. Audio Output

As shown in FIG. 1, Block S150 of the method S100 recites outputting the processed audio signal at the connected audio output device. Block S150 functions to output an electrical (analog or digital) signal that is converted into sound at a speaker within the connected audio device. For example, Block S140 can generate the processed audio signal locally on the user's mobile computing device, and Block S150 can output the processed audio signal as an analog signal through an audio jack integrated into the mobile computing device and connected to the audio device (e.g., a set of headphones), wherein a speaker within the audio device converts the analog signal into sound for the user. In another example, Block S140 can generate the processed audio signal remotely on a computer network and then stream the processed audio signal to the user's mobile computing device, such as over a Wi-Fi or cellular connection, and Block S150 can wirelessly transmit the processed audio signal as an digital signal to the audio device, such as over Bluetooth, wherein a speaker within the audio device converts the digital signal into sound for the user. In yet another example, Blocks S106, S110, S120, S130, S140, and S150 execute on the peripheral device connected to the user's mobile computing device and to the audio device, wherein Block S110 receives the audio signal over a wired (or wireless) connection to the mobile computing device, Block S140 generates the processed audio signal locally, and Block S150 outputs the processed audio signal over an integrated audio jack connected to the audio device (e.g., a set of headphones). Thus, Block S150 can substitute the audio signal for the processed audio signal at an output to the audio device. In particular, Block S150 can output the processed audio signal substantially in real-time with the audio signal.

Block S150 can additionally or alternatively output and/or transmit (e.g., wireless) the processed audio signal to a standalone speaker, a home, car, or other stereo system, a headset, an external mobile computing device (e.g., another user's phone), and/or to any other audio output device in communication with the user's mobile computing device, in communication with the peripheral device, and/or with a vicinity of the user.

Figure 4:
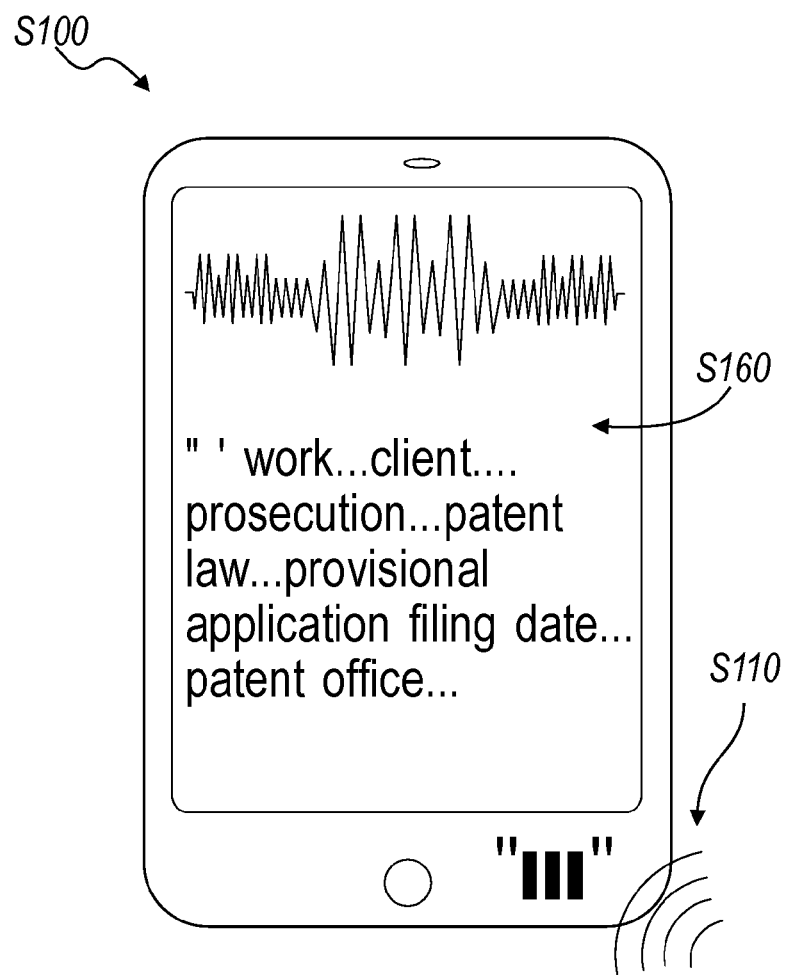
FIG. 4 is a graphical representation in accordance with one variation of the method.

As shown in FIG. 4, one variation of the method S100 further includes Block S160, which recites transcribing the audio signal into a stream of text and displaying the stream of text on the mobile computing device substantially in real-time within the audio signal. Generally, Block S160 functions to implement audio-to-text transcription methods or techniques to identify one or more words or phrases in the audio signal and to make the one or more words or phrases visually available to the user. Because context and meaning can be more easily and more quickly comprehended when read as opposed to heard, Block S160 can enable the user to identity the context (and content) of speech captured in the audio signal without necessitating replay of a past portion of the audio signal. In one implementation, Block S160 transcribes all words identified in speech captured in the audio signal and renders these words in text format on a display of the user's computing device (e.g., smartphone) executing other Blocks of the method S100. In another implementation, Block S160 filters identified words in the audio signal down to keywords renders these keywords in text format on the display, as shown in FIG. 4. In this implementation, Block S160 can enable the user to identify context of the speech by accessing keywords, which may be more efficient, quicker, and/or easier for the user to comprehend quickly than reading a substantially complete transcription. However, Block S160 can function in any other way to transcribe all or a portion of language in the audio signal and to display the transcribed portion of the audio signal on a display of the user's computing device.

7. Other Users

In one variation of the method S100, once a second user completes a hearing test and a hearing profile is thus generated for the second user as described above, the method S100 identifies a change in an environmental condition proximal the second user, such as by analyzing a microphone output, a GPS sensor output, and/or an accelerometer output, etc. within a smartphone carried by the second user. Thus, when a change in an environmental condition proximal the user similar to a change in environmental condition stored in the database is identified, Block S140 can automatically apply a change to the particular sound profile, to the user's hearing profile, and/or to the composite output profile to anticipate a manual input by the user based on a detected change in environmental condition similar to a detected change in an environmental condition proximal the second user and tagged with feedback from the second user. For example, if the method S100 identifies a change in local sound response proximal the second user (e.g., by interfacing with a microphone within a smartphone associated with the second user), Block S140 can apply this feedback from the second user to the user by automatically adjusting an EQ setting of the user's current composite output profile to mimic the manual EQ setting change entered by the second user. Block S140 can therefore respond to changing environmental conditions proximal the user substantially in real-time by automatically applying changes to the user's current hearing profile, sound profile, or composite output profile based on feedback from other users who previously experienced similar changes in local environmental conditions.

In this variation, Block S140 can also apply manually-entered audio output changes from other users to the user's composite output profile based on a hearing profile of the user and/or a demographic of the user. For example, Block S140 can apply manually-entered audio output changes to the user's composite output profile only for feedback entered by other users with hearing abilities similar to that of the user (e.g., based on similarities in the user's hearing test and hearing tests of other users). In another example, Block S140 applies manually-entered audio output changes to the user's composite output profile only for feedback submitted by other users within the same age bracket and of the same gender as the user.

Block S140 can implement similar techniques to apply manually-entered audio output changes by other users to the user's composite output profile based on a change in the user's location, entry of the user into a different space of known location or sound response, a change in proximity of the user to other users (e.g., based on GPS locations of smartphones associated with other users), and/or a change in the user's activity (e.g., from working at a desk to walking, from exercising to driving), etc. For example, Block S130 can collect feedback from various users before, during, and/or after such changes and store this feedback with corresponding changes, and Block S140 can later apply this feedback in the form of automatic (e.g., real-time) adjustment of the user's composite output profile when similar changes of, by, or proximal the user occur. However, Blocks of the method S100 can function in any other way to dynamically modify the user's composite output profile in response to a changing condition of or proximal the user.

Additionally or alternatively, after the user completes a first hearing test, Block S130 can collect user location data, environmental data, and/or ambient (e.g., noise) conditions proximal the user over time. The method S100 can further apply these data to characterize common "noise conditions" proximal the user (e.g., common sounds or noises recorded at the user's mobile computing device), such as based on time of day, day of the week, month, season, user location, etc. When the user completes a subsequent hearing test, Block S104 and/or Block S140 can retrieve feedback from other users associated with similar noise conditions and then generate an updated hearing profile for the user based on such feedback. The updated hearing profile can thus incorporate conditional hearing profile elements that enable automatic (i.e., dynamic) adjustment of the composite output profile for the user (e.g., without necessitating perpetual access to a remote database containing changes in environmental conditions and associated feedback tags from other users). For example, Block S104 can generate the user's hearing profile that inherently incorporates environmental changes and feedback from other users through "if . . . then . . . " statements defined within the user's hearing profile. Yet alternatively, Block S140 can update the user's hearing profile over time, such as additional user location data, environmental data, and/or ambient conditions proximal the user are collected over time (rather than in response to completion of a new hearing test by the user). However, the method S100 can function in any other way to implement feedback from other users into the user's hearing profile and/or into a composite output profile for the user.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for augmenting sound, comprising:
   at a mobile computing device and a connected audio output device, outputting a tone in a hearing test, wherein outputting the tone includes outputting a first audible tone comprising a first frequency, recording a first volume adjustment for the first audible tone by the user, outputting a second audible tone comprising a second frequency, recording a second volume adjustment for the second audible tone by the user;
   based on a response to the tone entered by a user, generating a hearing profile for the user and corresponding to the mobile computing device and the connected audio output device, wherein generating the hearing profile comprises selecting a particular hearing model from a set of hearing models based on a difference between the first volume adjustment and the second volume adjustment, each hearing model in the set of hearing models comprising a hearing test result corresponding to a previous patient, generating the hearing profile for the user based on the particular hearing model result, and associating the hearing profile with an identifier of the mobile computing device, associating the hearing profile with an identifier of the connected audio output device, and storing the hearing profile in an account assigned to the user;
   receiving an audio signal at the mobile computing device;
   qualifying the audio signal as a particular audio type from a set of audio types;
   selecting, from a set of sound profiles, a particular sound profile corresponding to the particular audio type;
   at the mobile computing device, transforming the audio signal into a processed audio signal according to both the particular sound profile and the hearing profile of the user; and
   outputting the processed audio signal at the connected audio output device.

2. The method of claim 1, wherein transforming the audio signal into the processed audio signal comprises retrieving the hearing profile from the account assigned to the user upon collection of the identifier of the mobile computing device and collection of the identifier of the connected audio output device.

3. The method of claim 1, wherein receiving the audio signal comprises receiving an analog signal from a microphone arranged in the connected audio device comprising a set of headphones, and wherein outputting the processed audio signal comprises outputting the processed audio signal through a speaker arranged in the set of headphones.

4. The method of claim 1, wherein qualifying the audio signal as the particular audio type comprises identifying the audio signal as an audio component of a phone call between the mobile computing device and a secondary device, wherein transforming the audio signal into the processed audio signal comprises attenuating a portion of the audio signal corresponding to a voice of the user and amplifying a portion of the audio signal received from the secondary device according to the particular sound profile.

5. The method of claim 1, further comprising transcribing the audio signal into a stream of text and displaying the stream of text on the mobile computing device substantially in real-time within the audio signal.

6. The method of claim 1, further comprising accessing an age and a gender of the user, wherein selecting the particular sound profile comprises selecting the particular sound profile previously elected by a second user of an age and a gender similar to the age and the gender of the user.

7. The method of claim 6, wherein identifying the age and the gender of the user comprises retrieving the age and the gender of the user from an online social networking system.

8. The method of claim 1, further comprising identifying a location of the user, upon retrieving the location from a global positioning system sensor of the mobile computing device, wherein selecting the particular sound profile comprises selecting the particular sound profile corresponding to the particular audio type for a location type comprising the location of the user.

9. The method of claim 1, wherein transforming the audio signal into the processed audio signal comprises applying a first equalizer setting specified by the particular sound profile and a second equalizer setting specified by the hearing profile of the user to the audio signal.

10. The method of claim 1, further comprising detecting an audio type of a sound output from the audio device, receiving an audio output adjustment from the user, generating a sound profile for the audio type based on the audio output adjustment from the user, and storing the sound profile with the set of sound profiles.

11. The method of claim 10, further comprising detecting an ambient noise condition, wherein receiving the audio output adjustment comprises receiving a volume adjustment from the user during output of the sound output from the connected audio output device, and wherein generating the sound profile for the audio type comprises generating the sound profile for the audio type based on the volume adjustment and associating the sound profile with the ambient noise condition, wherein selecting the particular sound profile comprises matching the audio type and the ambient noise condition of the sound profile to the audio signal.

12. The method of claim 1, further comprising receiving an audio output adjustment from the user during playback of the processed audio signal and modifying the particular sound profile based on the audio output adjustment.

13. A method for augmenting sound, comprising:
at a mobile computing device and a connected audio output device, outputting a tone in a hearing test, wherein outputting the tone includes outputting a first audible tone comprising a first frequency, recording a first volume adjustment for the first audible tone by the user, outputting a second audible tone comprising a second frequency, recording a second volume adjustment for the second audible tone by the user;
at a computing system, generating a hearing profile associated with a user, wherein generating the hearing profile comprises selecting a particular hearing model from a set of hearing models based on a difference between the first volume adjustment and the second volume adjustment, each hearing model in the set of hearing models comprising a hearing test result corresponding to a previous patient, generating the hearing profile for the user based on the particular hearing model result, and associating the hearing profile with an identifier of a mobile computing device of the user, associating the hearing profile with an identifier of a connected audio output device in communication with the mobile computing device, and storing the hearing profile in an account assigned to the user;
at the connected audio output device, receiving the hearing profile from the mobile computing device upon collection of the identifier the mobile computing device and collection of the identifier from the connected audio output device;
receiving an audio signal from the mobile computing device;
qualifying the audio signal as a particular audio type from a set of audio types;
selecting, from a set of sound profiles, a particular sound profile corresponding to the particular audio type;
transforming the audio signal into a processed audio signal according to both the particular sound profile and the hearing profile of the user; and
outputting the processed audio signal at an output of the connected audio output device in near real-time with reception of the audio signal at the mobile computing device.

14. The method of claim 13, wherein receiving the hearing profile from the mobile computing device comprises wirelessly downloading the hearing profile from the mobile computing device.

15. The method of claim 13, wherein receiving the audio signal from the mobile computing device comprises receiving the audio signal over an audio output jack within the mobile computing device.

16. The method of claim 13, wherein outputting the processed audio signal comprises substituting the audio signal for the processed audio signal at the output of the connected audio output device in communication with an external audio output device.

17. The method of claim 13, wherein qualifying the audio signal as the particular audio type comprises selecting the particular audio type from a set of audio types comprising music, speech, and ambient noise.

18. A method for augmenting sound, comprising:
at a mobile computing device and a connected audio output device, outputting a tone in a hearing test wherein outputting the tone includes outputting a first audible tone comprising a first frequency, recording a first volume adjustment for the first audible tone by the user, outputting a second audible tone comprising a second frequency, recording a second volume adjustment for the second audible tone by the user;
based on a response to the tone entered by a user, generating a hearing profile for the user and corresponding to the mobile computing device and the connected audio output device, wherein generating the hearing profile comprises selecting a particular hearing model from a set of hearing models based on a difference between the first volume adjustment and the second volume adjustment, each hearing model in the set of hearing models comprising a hearing test result corresponding to a previous patient, generating the hearing profile for the user based on the particular hearing model result, and associating the hearing profile with an identifier of the mobile computing device, associating the hearing profile with an identifier of the connected audio output device, and storing the hearing profile in an account assigned to the user;

receiving an audio signal at the mobile computing device;

qualifying the audio signal as a particular audio type from a set of audio types;

identifying a location of the user, upon retrieving the location from a global positioning system sensor of the mobile computing device;

selecting, from a set of sound profiles, a particular sound profile corresponding to the particular audio type, wherein selecting the particular sound profile comprises selecting the particular sound profile corresponding to both the particular audio type and a location type comprising the location of the user;

at the mobile computing device, transforming the audio signal into a processed audio signal according to both the particular sound profile and the hearing profile of the user; and outputting the processed audio signal at the connected audio output device in near real-time with reception of the audio signal at the mobile computing device.

\* \* \* \* \*